United States Patent
Rousseau et al.

(10) Patent No.: US 8,995,063 B2
(45) Date of Patent: Mar. 31, 2015

(54) OPTICAL DEVICE WITH ADJUSTABLE OPTICAL SURFACE

(75) Inventors: Benjamin Rousseau, Charenton Le Pont (FR); Thierry Bonnin, Charenton Le Pont (FR); Jean Taboury, Sceaux (FR); Raymond Mercier, Antony (FR); Sylvain Perrot, Palaiseau (FR)

(73) Assignee: Essilor International (Compagnie Generale D'Optique), Charenton le Pont (FR)

( * ) Notice: Subject to any disclaimer, the term of this patent is extended or adjusted under 35 U.S.C. 154(b) by 1099 days.

(21) Appl. No.: 13/056,546

(22) PCT Filed: Jul. 24, 2009

(86) PCT No.: PCT/EP2009/059602
§ 371 (c)(1),
(2), (4) Date: Jun. 26, 2012

(87) PCT Pub. No.: WO2010/012665
PCT Pub. Date: Feb. 4, 2010

(65) Prior Publication Data
US 2014/0071541 A1 Mar. 13, 2014

(30) Foreign Application Priority Data
Jul. 28, 2008 (EP) .................................. 08305429

(51) Int. Cl.
G02B 15/14 (2006.01)
G02B 3/14 (2006.01)
G02B 26/08 (2006.01)
A61F 2/16 (2006.01)

(52) U.S. Cl.
CPC ............. G02B 3/14 (2013.01); G02B 26/0825 (2013.01); *A61F 2/1635* (2013.01)

USPC .......................................................... 359/666

(58) Field of Classification Search
USPC .......................................................... 359/666
See application file for complete search history.

(56) References Cited

U.S. PATENT DOCUMENTS

| 5,203,788 A | 4/1993 | Wiley |
| 6,317,229 B1 | 11/2001 | Otterson |
| 6,949,093 B1 | 9/2005 | Peyman |
| 2004/0169932 A1* | 9/2004 | Esch et al. ..................... 359/665 |
| 2005/0157413 A1* | 7/2005 | Oshima et al. ................ 359/879 |

(Continued)

FOREIGN PATENT DOCUMENTS

| JP | 10-2006609 | 8/1998 |
| WO | WO 01/84210 | 11/2001 |
| WO | WO 2004/052242 | 6/2004 |

(Continued)

*Primary Examiner* — James Jones
(74) *Attorney, Agent, or Firm* — Cozen O'Connor

(57) ABSTRACT

An adjustable optical device comprising at least a deformable optical surface activated by linear fluidic actuators comprising: a material layer comprising an upper surface on which the optical surface is provided and a bottom surface; an actuator layer comprising a plurality of linear fluidic actuators separated by at least one cavity, where at least one linear fluidic actuator is a pillar extending in the actuation direction (L) which is non parallel to the bottom surface of the material layer, said pillar comprising a wall delimiting an internal cavity and where an upper surface of said pillar is continuously linked to a zone of the bottom surface of the material layer; fluidic inlets suitable for introducing a fluid in at least one internal cavity of a pillar linear fluidic actuator.

16 Claims, 11 Drawing Sheets

(56) References Cited

U.S. PATENT DOCUMENTS

2007/0030573 A1 2/2007 Batchko et al.
2007/0263293 A1 11/2007 Batchko et al.

FOREIGN PATENT DOCUMENTS

| WO | WO 2007/005778 | 1/2007 |
| WO | WO 2007/047529 | 4/2007 |

* cited by examiner

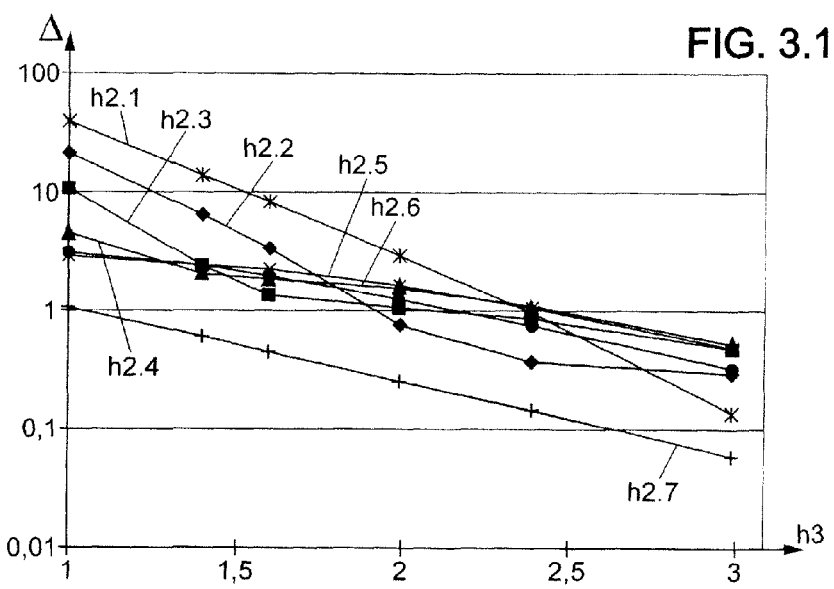
FIG. 3.1
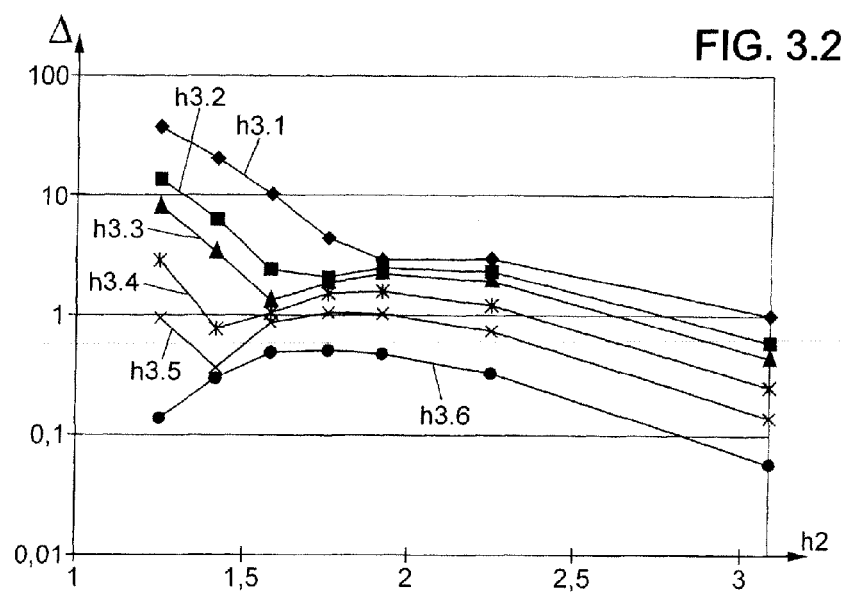
FIG. 3.2

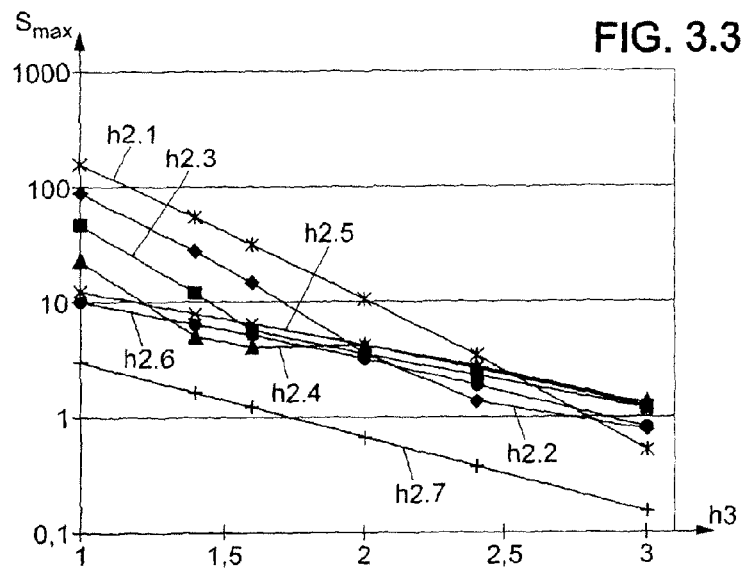
FIG. 3.3
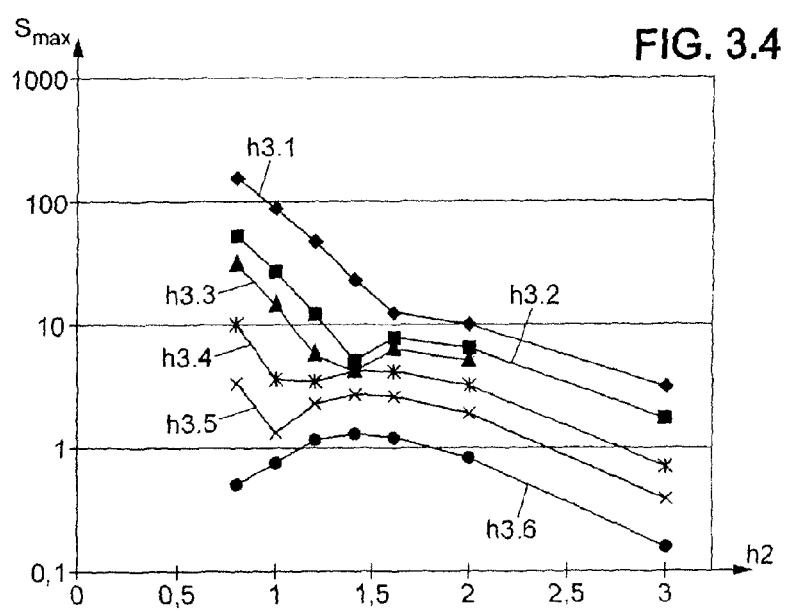
FIG. 3.4

OPTICAL DEVICE WITH ADJUSTABLE OPTICAL SURFACE

RELATED APPLICATIONS

This is a U.S. National Phase Application under 35 USC 371 of International Application PCT/EP2009/059602 filed on Jul. 24, 2009.

This application claims the priority of European application no. 08305429.6 filed Jul. 28, 2008, the entire content of which is hereby incorporated by reference.

FIELD OF THE INVENTION

The present invention relates to optical devices with at least one adjustable optical surface. More particularly, the present invention relates to optical devices where at least one optical surface can be in situ modified thanks to a plurality of deformable zones activated by fluidic means.

According to the present invention an "adjustable optical surface" is a surface suitable for transmitting or reflecting the light which geometrical characteristics may be changed so as to afford a plurality of optical characteristics.

BACKGROUND OF THE INVENTION

Known optical devices with an adjustable optical surface are for example adjustable or variable mirrors that are readily formable and can be changed into various configurations where an elastic or flexible material having one surface functioning as a reflecting surface can be bent thanks to actuation means. According to known embodiments, the flexible mirror is mounted in a frame and distributed load and/or axial loads are applied to the flexible mirror thanks to mechanical means such as screws or pins.

Other known optical devices with at least one adjustable surface are lenses, such as for example intra ocular implants. Said implants include a synthetic or organic material which may be adaptable by ablation by a laser beam and/or may be increased or decreased in volume and/or in refractive index when irradiated with energy such as light at a particular wave length, microwaves or thermal energy. Such an implant may be used to modify the curvature of a live cornea when implanted therein and be suitable for correcting eyes suffering from hypermetropy, myopia astigmatism or cataract. Although the surface of the implant can be shaped to a desired surface, once the desired surface is obtained it is no more possible, or at least very hard, to modify the implant surface.

In view of the foregoing, it would be desirable to develop optical devices with at least one optical surface that can be adjusted and finely tuned and also be actuated in a reversible way to provide a plurality of complex optical functions.

SUMMARY OF THE INVENTION

One object of the present invention is to improve fine tuning of optical device with at least one adjustable surface.

This object is obtained according to an aspect of the invention by an adjustable optical device comprising at least a deformable optical surface activated by linear fluidic actuators comprising:
  a material layer comprising an upper surface on which the optical surface is provided and a bottom surface;
  an actuator layer comprising a plurality of linear fluidic actuators separated by at least one cavity, where at least one linear fluidic actuator is a pillar extending in the actuation direction (L) which is non parallel to the bottom surface of the material layer, said pillar comprising a wall delimiting an internal cavity and where an upper surface of said pillar is continuously linked to a zone of the bottom surface of the material layer;
  fluidic inlets suitable for introducing a fluid in at least one internal cavity of a pillar linear fluidic actuator.

According to the present invention and thanks to fluidic actuation of a material layer comprising an upper surface on which an optical surface is provided, fine tuning of the geometrical characteristics of the optical surface is possible. Furthermore thanks to the continuous link between the upper surface of the pillar linear fluidic actuators and zones of the bottom surface of the material layer, it is possible to push or to pull the optical surface thus allowing shaping rapidly and reversibly a very wide range of complex surfaces.

According to an embodiment of the present invention, the actuation direction (L) is perpendicular to the bottom surface of the material layer.

According to another embodiment of the present invention, the actuation direction (L) is tilted relatively to the bottom surface of the material layer.

According to an embodiment of the present invention, the adjustable optical device comprises a plurality of pillar linear fluidic actuators arranged in the same actuation direction (L).

According to an embodiment of the present invention, the adjustable optical device comprises a plurality of pillar linear fluidic actuators arranged in a plurality of actuation directions.

According to an embodiment of the present invention, the pillar linear fluidic actuator(s) and the material layer are made continuously of the same material so as to form a sole continuous part.

According to another embodiment of the present invention, the upper surface of the pillar linear fluidic actuator(s) is continuously fixed to the zone of the bottom surface of the material layer. According to an embodiment, said upper surface of the pillar linear fluidic actuator(s) is sticked or glued to the zone of the bottom surface of the material layer. Other suitable continuous fixing means may be used.

According to different embodiments of the present invention that may be combined:
  the pillar linear fluidic actuator comprises a lower part consisting of the wall and the internal cavity and an upper part situated between the pillar upper surface and the pillar lower part;
  the pillar linear fluidic actuator has a cylindrical external surface which axis extends in the actuation direction L;
  the internal cavity is a cylinder which axis extends in the actuation direction L;
  the thickness of the pillar linear fluidic actuator's wall is between 0.1 to 2 mm, as for an example equal or greater to 0.25 mm and/or equal or less to 0.75 mm;
  the height ratio h1/h2 is comprised between 0.2 and 10, as for an example equal or greater to 0.5 and/or equal or less to 2, where h1 is the highest dimension of the internal cavity at rest according to the L direction and h2 is the distance at rest from the top of the upper surface of the internal cavity to the pillar's upper surface according to the L direction;
  the layer thickness ratio h3/h4 is comprised between 0.1 and 1, as for an example equal or greater to 0.2 and/or equal or less to 0.5, where h3 is the highest dimension at rest of the material layer according to the L direction and h4 is the highest dimension at rest of the actuator layer according to the L direction;
  h3 is comprised between 1 to 10 mm as for an example is equal or greater to 2 mm and/or equal or less to 5 mm;

the actuator layer is arranged on a substrate layer comprising the fluidic inlets;

the pillar linear fluidic actuators are arranged so as to form an array.

According to an embodiment of the present invention the optical surface is a light reflective surface. Said adjustable optical device can be used as an adjustable mirror. According to said embodiment, the fluid can be a liquid or a gas, as for example compressed air.

According to another embodiment of the present invention, the adjustable optical device comprises at least two optical surfaces where at least one of said surfaces is actuated by an actuator layer through a material layer and wherein said optical device is light transmissive. Said adjustable optical device can be used as a lens, as for example as an ophthalmic lens or as an intraocular ocular lens. According to said embodiment, the fluid is preferably a liquid which index of refraction matches the solid structure.

Another aspect of the present invention is directed to a method for adjusting a deformable optical surface of a previously mentioned adjustable optical device wherein a plurality of fluidic pressures (P1, P2, . . . ) is provided within the internal cavities of the pillar linear fluidic actuators and a constant pressure Po is provided within the cavity(ies) which separate(es) the pillar linear fluidic actuators.

Another aspect of the present invention is directed to a method for providing a lens for a wearer comprising the steps of:

providing a previously mentioned adjustable optical device to the wearer;

adjusting the fluidic pressures (P1, P2 . . . ) of a plurality of internal cavities of the pillar linear fluidic actuators so as to obtain a desired optical system.

The present invention is also directed to a method for testing a lens for a wearer comprising the steps of:

providing a previously mentioned adjustable optical device to a wearer;

adjusting the fluidic pressures (P1, P2 . . . ) of a plurality of internal cavities of pillar linear fluidic actuators so as to obtain a first optical system;

asking for the wearer's opinion;

modifying the fluidic pressures (P1, P2 . . . ) of a plurality of internal cavities of pillar linear fluidic actuators so as to obtain a second optical system;

asking for the wearer's preference.

Another aspect of the present invention relates to a method for manufacturing a previously mentioned adjustable optical device comprising the steps of:

providing a mould with a plurality of closed shapes defining the external contours of the cavities of the actuator layer;

providing at least the wall material by moulding.

According to the present invention a fluid can be a liquid or a gas.

In the frame of the present invention, the wordings "upper", "bottom" or "lower", "on", "under" indicate positions relative to an axis perpendicular to a deformable optical surface at rest that can be activated by a plurality of fluidic linear actuators. Said deformable optical surface is purely conventionally considered as an upper surface, without any prejudice of its actual spatial position.

According to an embodiment the deformable optical surface is flat at rest.

According to another embodiment the deformable optical surface is curved at rest. Its shape can be spherical, cylindrical or of complex geometry.

When the deformable optical surface is curved at rest, one have to consider positions relative to a plurality of axis, where each axis is locally perpendicular to the deformable optical surface at rest.

According to an embodiment of the present invention, the pillars directions have the same orientation than the axis perpendicular to the deformable optical surface at rest.

The deformable optical surface is at rest when the pressure in all the cavities of the actuator layer is identical, as for an example is equal to the atmospheric pressure.

According to the present invention, the wording "continuously" means that the link between two continuously linked surfaces is stiff and complete meaning that each point of one of said surfaces follows corresponding point of the other surface when it moves whatever the movement direction is.

According to the present invention, the wording "pillar" is a part onto which another part may be arranged. As for an example a pillar according to the present invention is an elongated part. According to non limiting embodiments, such a pillar may be of constant section, such as for examples a circle, a square, a hexagon; it may also be of variable sections, or be formed by several parts of constant sections with at least two different sections.

BRIEF DESCRIPTION OF THE DRAWINGS

The novel features of this invention, as well as the invention itself, both as to its structure and its operation, will be best understood from the accompanying non limiting drawings and examples, taken in conjunction with the accompanying description, in which like reference characters refer to similar parts, and in which:

FIGS. 3.1 to 3.4 show surface parameters of displaced optical surfaces thanks to embodiments of adjustable optical devices of the invention;

FIGS. 7-1 to 7-10 show different embodiments of a pillar linear fluidic actuator according to the present invention;

FIG. 8 shows another partial diagrammatic section of an adjustable optical device according to the present invention;

FIGS. 9 and 10 show moulds and injection moulding devices that can be used to manufacture components of an optical device according to the present invention.

DETAILED DESCRIPTION OF THE DRAWINGS

Skilled artisans appreciate that elements in the figures are illustrated for simplicity and clarity and have not necessarily been drawn to scale. For example, the dimension of some of the elements in the figures may be exaggerated relative to other elements to help improve the understanding of the embodiment of the present invention.

Figure 1:
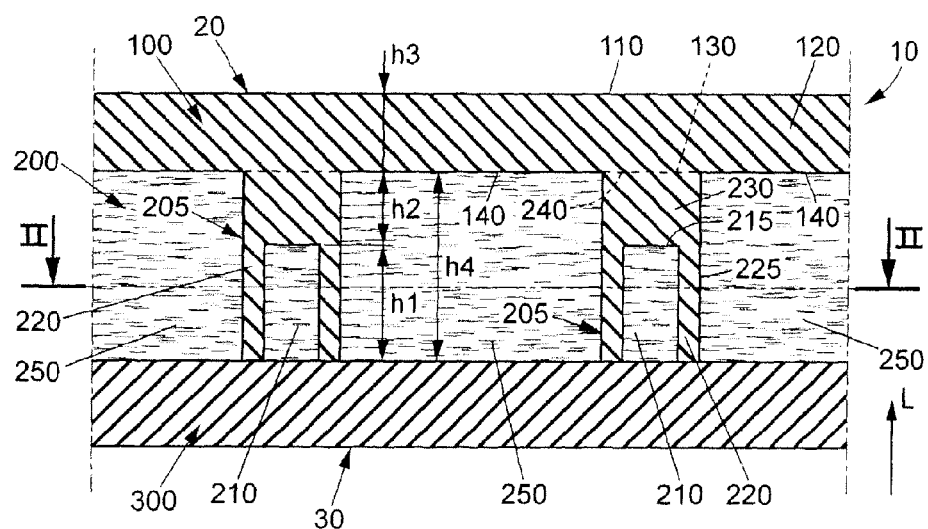
FIG. 1 shows a partial diagrammatic section of an adjustable optical device according to an embodiment of the present invention.

The adjustable optical device 10 of FIG. 1 comprises three layers of material stacked one upon the other. The bottom layer 300 is a non deformable layer of constant thickness acting as a substrate. The intermediate layer 200 comprises a plurality of pillar linear fluidic actuators 205. The thickness of said actuator layer 200 is at rest h4. The upper layer 100 is a deformable material layer which thickness at rest is h3. According to this embodiment, the material layer 100 consists of only one material layer 120. According to other embodiments (not shown), the material layer 100 consists of a plurality of material layers stacked one upon the others.

According to a non-limiting embodiment, the plurality of pillar linear fluidic actuators 205 forms an array.

According to a non-limiting embodiment, the distance between the centers of the pillar linear fluidic actuators is constant. Said distance may be for example comprised between 2 mm and 20 mm, as for example equal or greater to 5 mm and/or equal or less than 10 mm.

The deformable material layer 100 comprises an upper surface 110 on which an optical surface 20 is provided. The optical surface 20 may be the surface 110 itself, or can be stacked on the surface 110 and, as for an example, be coated on said surface.

The surface 20 may be a light transmissive or a light reflective surface.

The adjustable optical device of FIG. 1 may be used as a mirror if surface 20 is a light reflective one or as a lens if surface 20 and layers 100, 200, 300 are made of light transmissive materials.

When the adjustable optical device of FIG. 1 is a lens, the substrate layer 300 is provided with an optical surface 30. Said optical surface 30 may be the bottom surface of the substrate layer 300 or can be stacked on said bottom surface and, as for an example, be coated on said surface.

According to a non-limiting embodiment, the bottom layer 300 is made of glass.

The actuator layer 200 comprises an array of pillar linear fluidic actuators 205 separated by one sole cavity 250. Each pillar linear fluidic actuator 205 comprises a wall 220 delimiting an internal cavity 210 in which a fluid can be provided. The pillars extend at rest in a L direction perpendicular to the bottom surface 130, 140 of the material layer 100. The L direction is the actuation direction. According to said embodiment, they extend at rest also perpendicularly to the optical surface 20.

A pillar linear fluidic actuator 205 comprises a lower part; consisting of the wall 220 and the cavity 210, and an upper part 230.

The height of a pillar linear fluidic actuator at rest is h4 and corresponds to the thickness of the actuator layer 200; the height of the lower part is h1 and the height of the upper part is h2, where h1+h2=h4. The upper part 230 is full and made of the same material as wall 220. The pillar linear fluidic actuator 205 has a cylindrical external surface 225 which axis extends in the L direction. The internal cavity 210 of a pillar linear fluidic actuator 205 is a cylinder which axis extends in the L direction. The upper surface 215 of the cavity 210 is flat.

Figure 2:
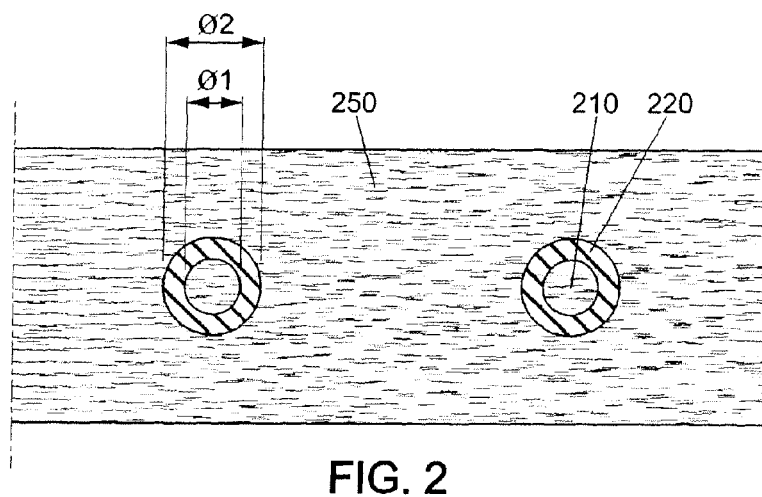
FIG. 2 shows a partial cross section of the optical device of FIG. 1 according to II-II section.

As shown on FIG. 2, the diameter of the cylindrical external surface 225 is φ2 and the diameter of the internal cylindrical cavity 210 is φ1.

The pillar linear fluidic actuator has an upper surface 240 contacting bottom surface zones 130 of the material layer 100. Said surface 240 is an upper actuation deformable surface and is suitable to induce a displacement in the actuation direction L.

According to the embodiment of FIG. 1, the pillar linear fluidic actuators 205 and the material layer 100 are continuously made of the same material. The link between upper surfaces 240 of the pillar linear fluidic actuators and bottom surface zones 130 of the material layer 100 is thus continuous.

It would also be possible to design discontinuously the pillar linear fluidic actuators 205 and the material layer 100 and to joint them continuously by sticking or gluing.

The substrate layer 300 comprises fluidic inlets (not represented here) in connexion with the internal cavities 210 of the pillar linear fluidic actuators 205.

Said fluidic inlets may be connected to fluidic control parts which may not be part of the optical device 10 itself. External fluid reservoirs and hydraulic systems can be connected to the fluidic inlets thanks to channels designed in the substrate layer 300.

According to an embodiment where the adjustable optical device is a lens, the substrate layer 300, the pillar linear fluidic actuators 205 and the material layer 100 are all made of light-transmissive materials, such as silicone, silicone polymeric material, acrylic polymeric material, hydrogel polymeric material or other materials as are known in the art of lenses. The fluid used in the pillar linear fluidic actuators is selected to have refractive index that met the materials of the substrate layer 300 and of the pillar linear fluidic actuators 205. Said fluid may be for example made of liquid silicones; acrylic oils; solid silicones and water solutions; liquid silicones and solid PMA. Thus the desired effect of index matching may be achieved so as to render the solid structure undetectable in a desired region of the light spectrum. According to an embodiment said region of the light spectrum is the visible range; according to other embodiments said region of the light spectrum can be part of the UV range or part of the lit range.

The deformable optical surface 20 can be adjusted thanks to varying the fluidic pressure within the internal cavities 210 of the pillar linear fluidic actuators 205.

When the pressure within an internal cavity 210 is higher than the pressure in the surrounding cavity 250, the upper surface 215 of the cavity pushes the material layer 100. When the pressure within an internal cavity 210 is lower than the pressure of the surrounding cavity 250, the upper surface 215 of the cavity pulls the material layer 100.

According to an embodiment of the present invention the value of h2 may be nil and the upper surface 215 of the cavity may contact directly the bottom surface zone 130 of the material layer 100.

According to another embodiment of the present invention the value of h2 is not nil and the upper part 230 of the pillar linear fluidic actuator transmits the deformation of the upper surface 215 of the cavity to the bottom surface zone 130 of the material layer 100. The inventors have demonstrated that said embodiment is of particular interest and allows smooth deformation of the material layer 100 and thus fine tuning of the deformable optical surface 20.

According to non limiting examples of adjustable optical devices of the present invention:

The pressure within the surrounding cavity 250 is the atmospheric pressure, Po;

The diameter of internal cylindrical cavity φ1 is 2 mm;

The diameter of cylindrical external surface of the wall φ2 is 3 mm;

The height h1 of the lower part of the pillar linear fluidic actuator, i.e. the height of the internal cavity 210 is 4 mm;

The height h2 of the upper part of the pillar linear fluidic actuator is chosen between 0.8 mm to 3 mm, namely chosen as following examples:

h2.1=0.8 mm;

h2.2=1 mm;

h2.3=1.2 mmm;

h2.4=1.4 mm;

h2.5=1.6 mm;
h2.6=2 mm;
h2.7=3 mm;

The height h3 of the material layer 100 is chosen between 1 mm to 3 mm, namely chosen as following examples:

h3.1=1 mm;
h3.2=1.4 mm;
h3.3=1.6 mm;
h3.4=2 mm;
h3.5=2.4 mm;
h3.6=3 mm;

The Young modulus of the material chosen for the pillar linear fluidic actuators 205 and the material layer 100 is 5000 N/m$^2$ and its Poisson's ratio is v=0.5.

Tests have been made to characterize the geometry of the optical surface 20 when actuating it with a constant pressure, comprised between 1 and 2 kPa according to the geometry, in all the cavities 210 of the pillar linear fluidic actuators 205 and providing a uniform mean displacement of 500 μm of the upper surface 215 of the internal cavity 210.

According to the present specification, pressures refer to relative pressure compared to atmospheric pressure. Thus P=0 means that the pressure value P is the atmospheric pressure.

Figures 1, 7:
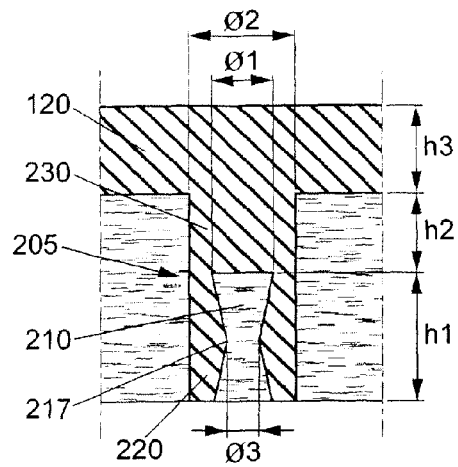
Figures 2, 7:
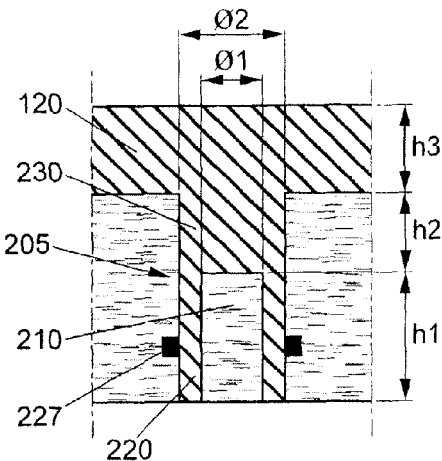
Figures 3, 7:
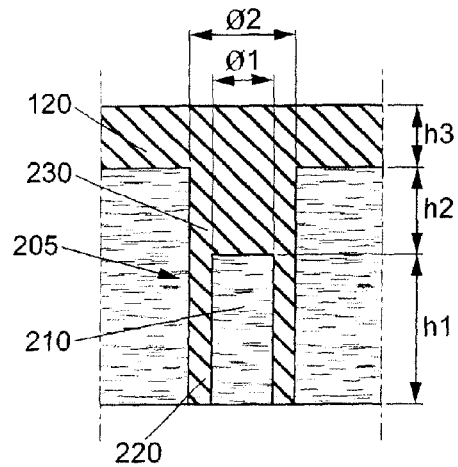
Figures 4, 7:
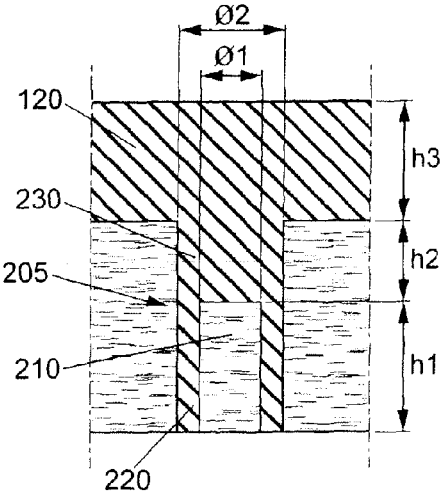
Figures 5, 7:
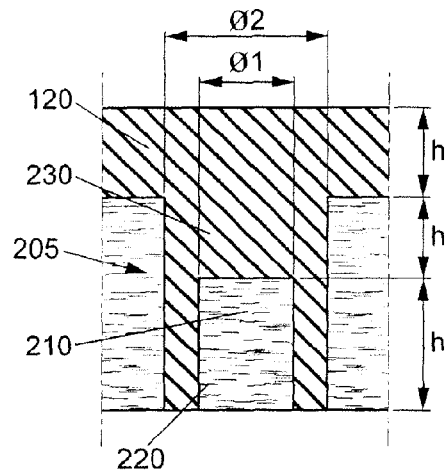
Figures 6, 7:
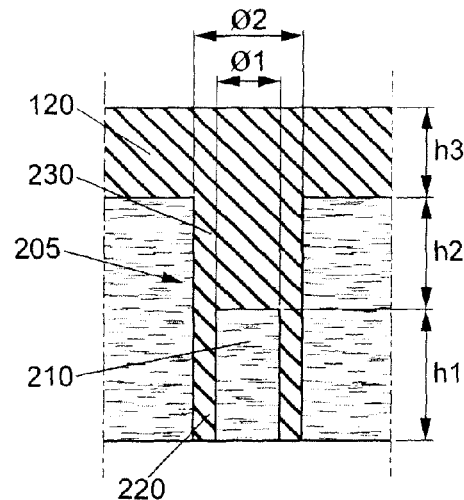
Figure 7:
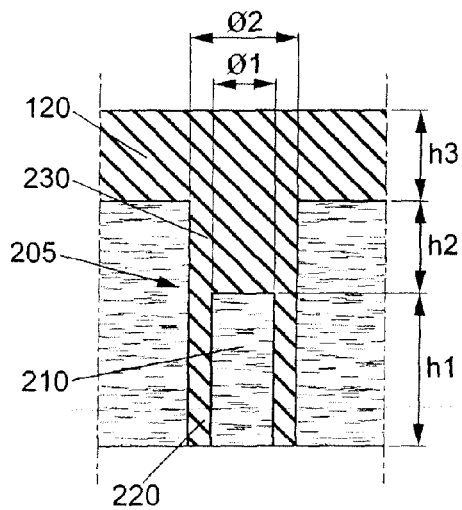

FIGS. 3.1 to 3.4 show the resulting optical surface 20 characteristics.

FIG. 3.1 shows the maximum peak to valley differences, Δ, in μm, between the actual optical surface position and the optical surface as it were translated from 500 μm as a function of the h3, for the 7 different values of h2, h2.1 to h2.7.

FIG. 3.2 shows the maximum peak to valley differences, Δ, in μm, between the actual optical surface position and the optical surface as it were translated from 500 μm as a function of h2, for the 6 different values of h3, h3.1 to h3.6.

FIG. 3.3 shows the maximum slope, Smax, in arc min, between the actual optical surface position and the optical surface as it were translated from 500 μm as a function of h3 for the 7 different values h2, h2.1 to h2.7.

FIG. 3.4 shows the maximum slope, Smax, in arc min, between the actual optical surface position and the optical surface as it were translated from 500 μm as a function of h2 for the 6 different values of h3, h3.1 to h3.6.

The man of the art is thus able to choose the geometrical parameters of the adjustable optical device according to the surface displacements and surface qualities he wishes.

It has been demonstrated that very low deformation levels can be reached, for example about 60 nm for h2=3 mm and h3=3 mm.

More complex surfaces have then been generated with preceding example where h2=h3=3 mm.

According to a first example, a square pillar array of linear fluidic actuators is used where firstly three and then four consecutive linear fluidic actuators are filled with fluid at different fluidic pressure in order to generate a slope on the deformable optical surface 20. The distance between the centers of the pillar linear fluidic actuators is 8 mm. Using three consecutive pillar linear fluidic actuators different pressures of 1; 2; 3 kPa make possible generating a slope of 22 mrad where the maximum slope variation is about 400 μrad.

Using four consecutive pillar linear fluidic actuator different pressures of 0; 1; 2; 3 kPa make possible generating a slope of 22 mrad where the maximum slope variation is about 500 μrad.

The maximum slope variation was reduced when adjusting the fluidic pressure of the pillar linear fluidic actuator: a slope of 22 mrad with a slope variation of about 460 wad was generated when using following pressures: 0; 1 kPa; 1.985 kPa; 2.985 kPa.

According to another example with the same optical device structure a parabolic surface was generated.

Figure 4:
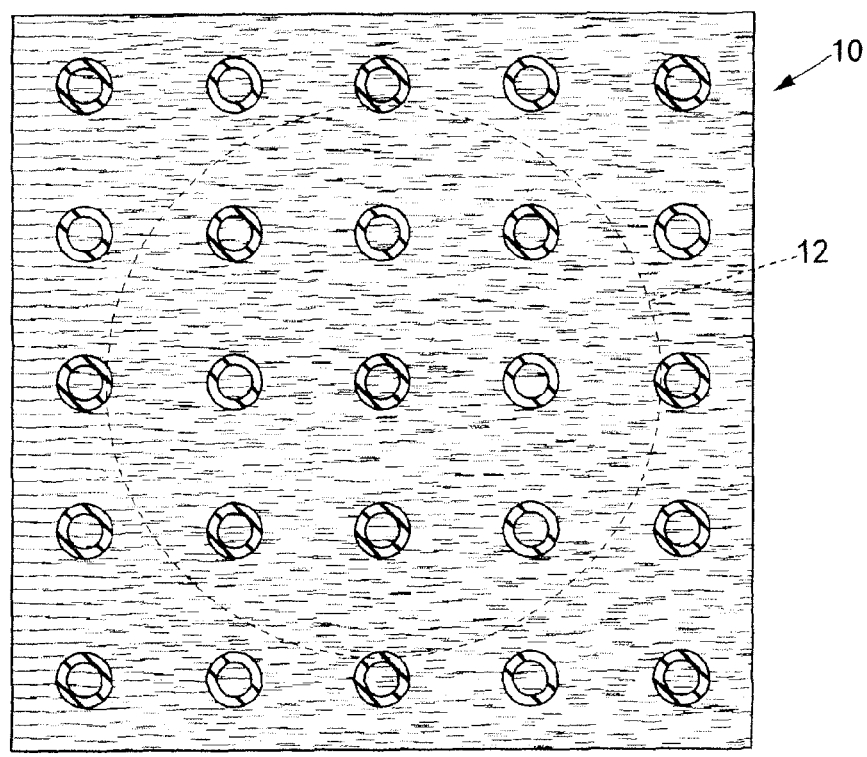
FIG. 4 shows an embodiment of the array of linear fluidic actuators according to the present invention.

FIG. 4 illustrates a square array consisting of 25 pillar linear fluidic actuators (with h2=h3=3 mm and a distance of 8 mm between the centers of the pillar linear fluidic actuators, according to preceding examples).

The pillar linear fluidic actuators are fed so as to generate a parabolic surface close to a spherical surface within circle 12 (30 mm diameter circle); optimised pressures range between 170 to 3800 Pa.

The deformable optical surface was parabolic with a top deformation of about 700 μm. The average curvature radius was 400 mm on a 30 mm diameter, the sag value was about 280 μm and the departure from sphere was about 1.8 μm RMS and 12.5 μm peak to valley.

Figure 5:
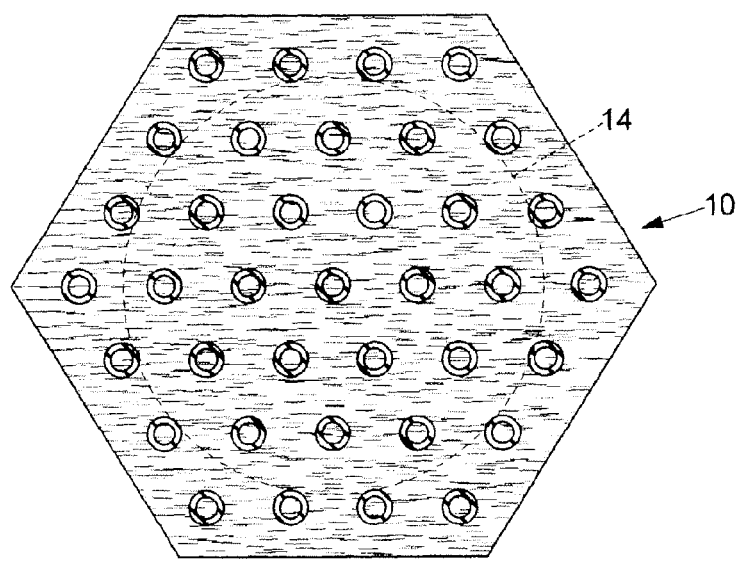
FIG. 5 shows another embodiment of the array of linear fluidic actuators according to the present invention.

FIG. 5 shows another pillar linear fluidic actuator spatial distribution where the array is hexagonal. 37 pillar linear fluidic actuators are arranged according to a hexagonal mesh and distance between the centers of the pillar linear fluidic actuators is 8 mm.

Figure 6:
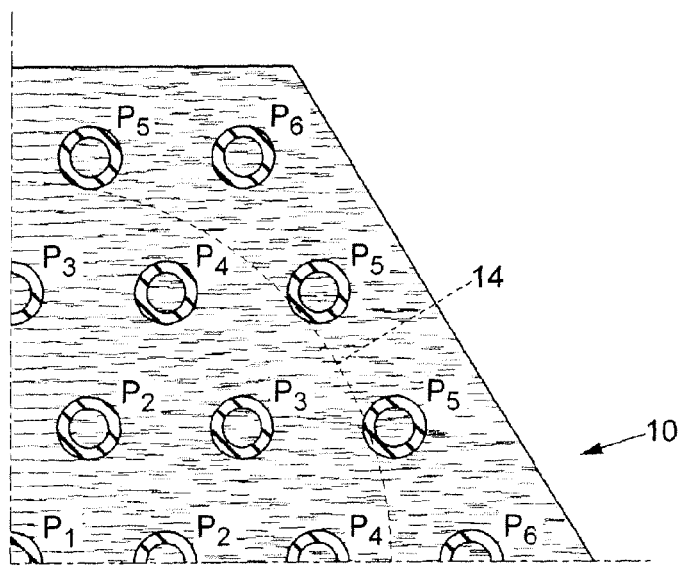
FIG. 6 shows an example of pressure repartition in linear fluidic actuators disposed according to FIG. 5.

FIG. 6 shows the pressure repartition used to generate a spherical optical surface within a circle 14 which diameter is 40 mm.

According to an example:

P1=4925 Pa;
P2=4283 Pa;
P3=3476 Pa;
P4=3064 Pa;
P5=1043 Pa;
P6=0.

The average radius of curvature of the best sphere of the obtained optical surface was 399 mm; peak to valley maximal departure of the surface was less than about 16 μm and slope defects were less than 10 mrad on the whole sphere surface (40 mm diameter). Said variations were significantly reduced when considering a reduced zone: peak to valley maximum departure from the best sphere was less than about 8 μm and slope defects were less than about 2.5 mrad for a 35 mm diameter zone.

Pressure data was then re-optimized to reduce the defects on the reduced 35 mm diameter and very small surface variations were obtained with to following pressure data:

P1=5014 Pa;
P2=4449 Pa;
P3=3546 Pa;
P4=3197 Pa;
P5=1267 Pa;
P6=0.

Peak to valley maximum variation was less than 5.6 μm and slope defects were less than about 2 mrad on the surface of the sphere according to a 35 mm diameter. Very smooth optical surface can then be obtained.

According to other examples of the present invention, even more complex optical surfaces were generated.

As for an example, a complex optical surface close to the one of a progressive addition lens (PAL) was generated using an array of pillar linear fluidic actuators according to FIG. 5, where the distance between the centers of the pillar linear fluidic actuators is 5 mm and the circle 14 has a 25 mm diameter.

Said complex surface can be described using 66 Zernike polynomial functions with the coefficients of Table 1, where N corresponds to the order of the consecutive Zernike polynomial functions and "coef" corresponds to the coefficient used for corresponding Zernike polynomial function to describe the present optical surface.

TABLE 1

| N | Coef (μm) |
|---|---|
| 1 | −0.199 |
| 2 | 0 |
| 3 | −0.591 |
| 4 | −56.974 |
| 5 | −0.601 |
| 6 | 0 |
| 7 | 0 |
| 8 | 0 |
| 9 | 76.826 |
| 10 | 34.907 |
| 11 | −36.451 |
| 12 | −10.461 |
| 13 | 10.661 |
| 14 | 0 |
| 15 | 0 |
| 16 | 0 |
| 17 | 0 |
| 18 | 0 |
| 19 | −9.126 |
| 20 | −10.775 |
| 21 | −12.248 |
| 22 | −3.571 |
| 23 | 8.730 |
| 24 | 2.098 |
| 25 | −1.832 |
| 26 | 0 |
| 27 | 0 |
| 28 | 0 |
| 29 | 0 |
| 30 | 0 |
| 31 | 0 |
| 32 | 0 |
| 33 | 2.481 |
| 34 | 2.951 |
| 35 | 2.501 |
| 36 | −2.697 |
| 37 | 0.840 |
| 38 | 1.422 |
| 39 | −2.250 |
| 40 | −0.506 |
| 41 | 0.859 |
| 42 | 0 |
| 43 | 0 |
| 44 | 0 |
| 45 | 0 |
| 46 | 0 |
| 47 | 0 |
| 48 | 0 |
| 49 | 0 |
| 50 | 0 |
| 51 | −0.822 |
| 52 | −1.099 |
| 53 | −0.391 |
| 54 | 1.054 |
| 55 | 0.116 |
| 56 | 0.101 |
| 57 | −0.384 |
| 58 | −0.561 |
| 59 | 0.889 |
| 60 | 0.191 |
| 61 | −0.490 |
| 62 | 0 |
| 63 | 0 |
| 64 | 0 |
| 65 | 0 |
| 66 | 0 |

Preceding examples demonstrate that an adjustable optical device comprising at least a deformable optical surface activated by linear fluidic actuators according to the present invention afford large displacements of the deformable optical surface. Said displacements of the deformable optical surface may be of several 100 μm and possibly more than a one mm. Said displacements are obtained with a very compact structure; the ratio between the maximum displacements of the deformable optical surface to the thickness of the linear fluidic actuator(s) is highly advantageous; according to a non limiting example, an order of magnitude of said ratio is 0.1, corresponding for example to a 5 mm linear fluidic actuator suitable to induce a 500 μm deformable optical surface displacement.

Several other parameters of optical devices according to the present invention were studied.

The geometry of the internal cavity 210 of pillar linear fluidic actuators 205 was studied in order to help designing optimum adjustable optical devices.

FIGS. 7.1 to 7.10 illustrate 10 different geometrical configurations, which are compared to the "standard" configuration according to FIG. 1.

The internal cavity 210 of FIG. 7.1 comprises a wall bulge 217 which internal diameter φ3 is 1.2 mm.

The wall 220 of FIG. 7.2 is restrained by a continuous ring 227.

The pillar's upper part 230 of FIG. 7.3 is higher than the one of FIG. 1 and the material layer 120 is thinner.

The pillar's upper part 230 of FIG. 7.4 is smaller than the one of FIG. 1 and the material layer 120 is thicker.

The internal diameter φ1 of FIG. 7.5 is greater than the one of FIG. 1.

The pillar's upper part 230 of FIG. 7.6 is higher than the one of FIG. 1 and the material layer 120 remains constant.

The height of the internal cavity 210 of FIG. 7.7 is higher than the one of FIG. 1 and the upper part and the material layer remain constant.

The form of the internal cavity 210 of FIG. 7.8 is modified compared to FIG. 1 and a concave surface 216 replaces the flat surface 215; a ring 232 is added in the upper part of the upper part 230.

The form of the internal cavity 210 of FIG. 7.9 is modified compared to FIG. 1 and a concave surface 216 replaces the flat surface 215.

The form of the internal cavity 210 of FIG. 7.10 is modified compared to FIG. 1 and a convex surface 217 replaces the flat surface 215

To determine the influence of the here above mentioned configuration on the optical surface actuation, five linear pillar linear fluidic actuators were fed with fluid at five different pressures, P1, P2, P3, P4, P5 so as to obtain a 22 mrad slope.

The resulting optical surfaces were characterized and the data are reported in Table 1 for 11 configurations (FIG. 1 and FIGS. 7.1 to 7.10).

The maximum peak to valley, differences, Δ (in μm), and the maximum slope variation, "slope max" are reported (in arc minutes).

An estimation of the stresses within the material according to the different configurations was performed; the maximum compression stresses $S_{ii}$ and the maximum shear stresses $S_{ij}$ are reported in Table 2.

One can notice that when the thickness, h3, of the material layer 120 increases, the optical surface defects generally decrease, but the fluidic pressures to be introduced into the internal cavity 210 have to increase to obtain the same optical surface slope.

TABLE 2

| | Geometrical parameter of the pillar linear fluidic actuator | | | | | Pressure values for obtaining a 22 mrd slope | | | | | Optical surface defects | Resulting stresses | | |
|---|---|---|---|---|---|---|---|---|---|---|---|---|---|---|
| | | | | | | | | | | | | Slope max | $S_{ii}$ max | $S_{ij}$ max |
| | Ø1 | Ø2 | h1 | h2 | h3 | P1 | P2 | P3 | P4 | P5 | Δ(μm) | (arcmin) | (N/m²) | (N/m²) |
| FIG. 1 | 2 | 3 | 4 | 3 | 3 | 0 | 1009 | 1994 | 2980 | 3987 | 1.10 | 1.73 | 13686 | 6542 |
| FIG. 7.1 | 2 | 3 | 4 | 3 | 3 | 0 | 752 | 1491 | 2231 | 2981 | 1.10 | 1.74 | 4805 | 3947 |
| FIG. 7.2 | 2 | 3 | 4 | 3 | 3 | 0 | 538 | 1063 | 1589 | 2126 | 1.41 | 2.23 | 5395 | 2520 |
| FIG. 7.3 | 2 | 3 | 5 | 3 | 2 | 0 | 964 | 1912 | 2861 | 3823 | 2.72 | 4.59 | 12984 | 6170 |
| FIG. 7.4 | 2 | 3 | 4 | 3 | 4 | 0 | 1012 | 1997 | 2983 | 3993 | 0.48 | 0.70 | 13707 | 6553 |
| FIG. 7.5 | 3 | 4 | 4 | 3 | 3 | 0 | 571 | 1118 | 1669 | 2234 | 2.86 | 4.16 | 8668 | 4817 |
| FIG. 7.6 | 2 | 3 | 4 | 4 | 3 | 0 | 1009 | 1995 | 2981 | 3989 | 0.99 | 1.56 | 13692 | 6545 |
| FIG. 7.7 | 2 | 3 | 5 | 3 | 3 | 0 | 971 | 1918 | 2866 | 3836 | 0.96 | 0.61 | 13028 | 6191 |
| FIG. 7.8 | 2 | 3 | 4.5 | 2.5 | 3 | 0 | 1307 | 2585 | 3860 | 5169 | 1.04 | 1.47 | 17681 | 8456 |
| FIG. 7.9 | 2 | 3 | 4.5 | 2.5 | 3 | 0 | 1308 | 2588 | 3863 | 5174 | 1.19 | 1.82 | 17697 | 8463 |
| FIG. 7.10 | 2 | 3 | 4.5 | 2.5 | 3 | 0 | 900 | 1779 | 2659 | 3557 | 1.10 | 1.73 | 12224 | 5850 |

According to said experiments, following ranges of parameters values may be considered as being suitable for obtaining adjustable optical devices with interning optical properties. It has to be noted that following ranges are not limiting the present invention and are given as illustrating examples:

Thickness of the pillar linear fluidic actuator is between 0.1 and 2 mm, as for an example equal or greater to 0.25 mm and/or equal or less than 0.75 mm.

Upper part height h3 is comprised between 1 and 10 mm, as for an example is equal or greater to 2 mm and/or equal or less to 5 mm.

The layer thickness ratio h3/h4 is comprised between 0.1 and 1, as for an example equal or greater to 0.2 and for equal or less to 0.5.

The height ratio h1/h2 is comprised between 0.2 and 10, as for an example equal or greater to 0.5 and/or equal or less to 2.

Said parameters ranges may be combined to select multi parameters adjustable optical device configurations.

Figures 7, 8:
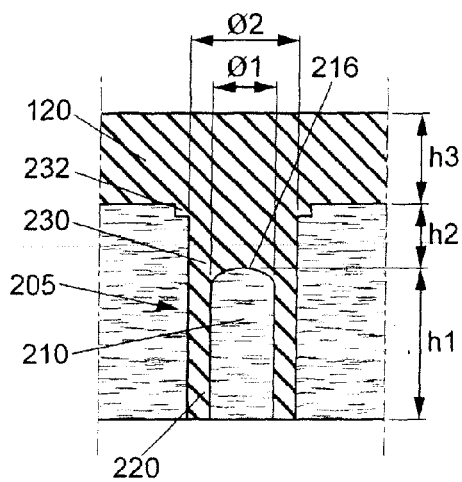

FIG. 8 illustrates another embodiment of the present invention where a second material 400 is arranged on the upper surface of the material layer 100. According to an embodiment, the material layer 400 is more rigid than the material layer 100 and is suitable to lower the surface defects of the deformable optical surface. Said deformable optical surface may be further smoothed thanks to material layer 400. One can note that the material layer 400 may have a different index of refraction than material layer 100 namely when the two said layers are parallel.

Figures 7, 8, 9:
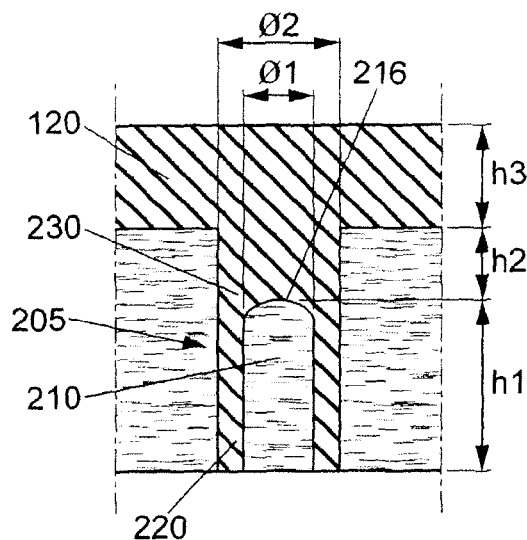

FIGS. 9 a-b and 10 a-b illustrate moulds and injection moulding devices that can be used to manufacture components of an adjustable optical device according to the invention.

FIGS. 9 a-b illustrate a mould 500 used to manufacture part of the substrate layer 300 where a full channel 530 and a full cylinder 540 are provided on a substrate plate 510. Full parts may be made of glass. A polymeric material is injected within the bottom substrate plate 510 and an upper plate 520.

Figures 7, 8, 9, 10:
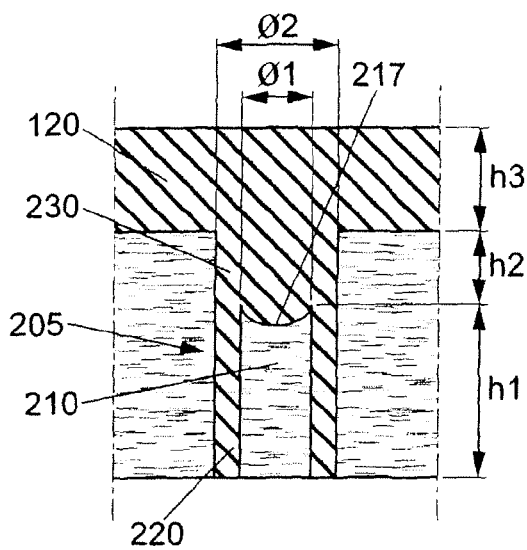
Figure 8:
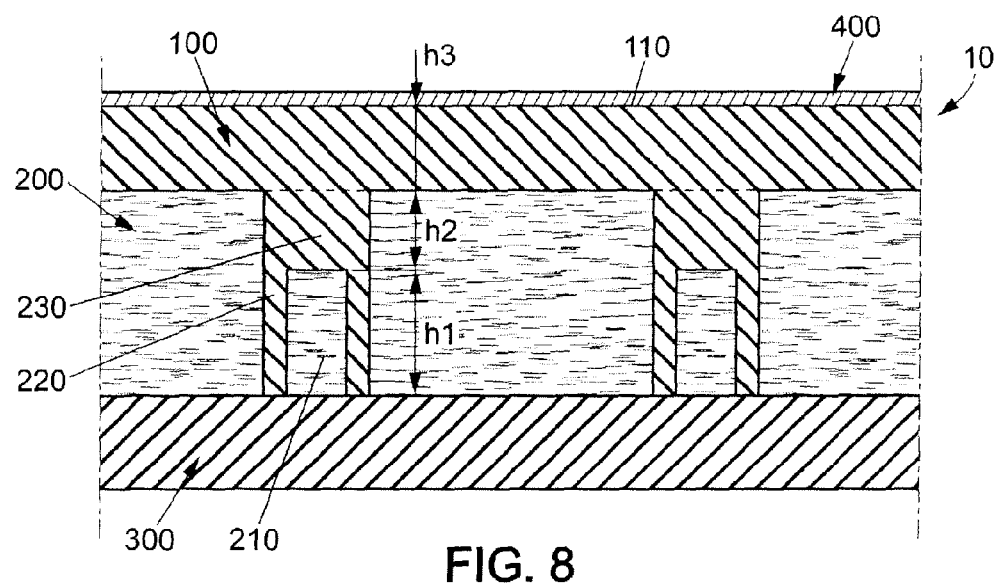
Figure 9A:
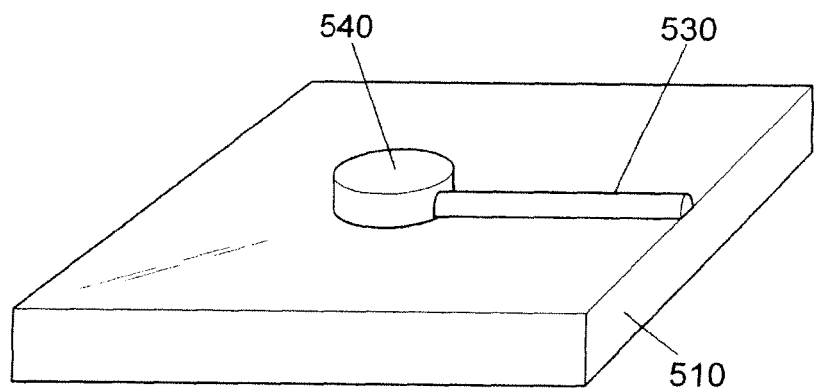
Figure 9B:
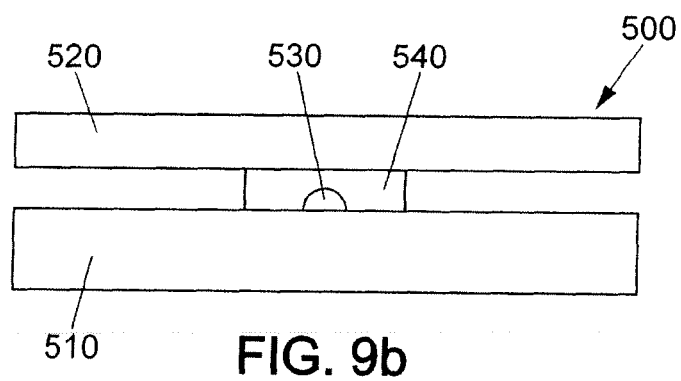
Figure 10A:
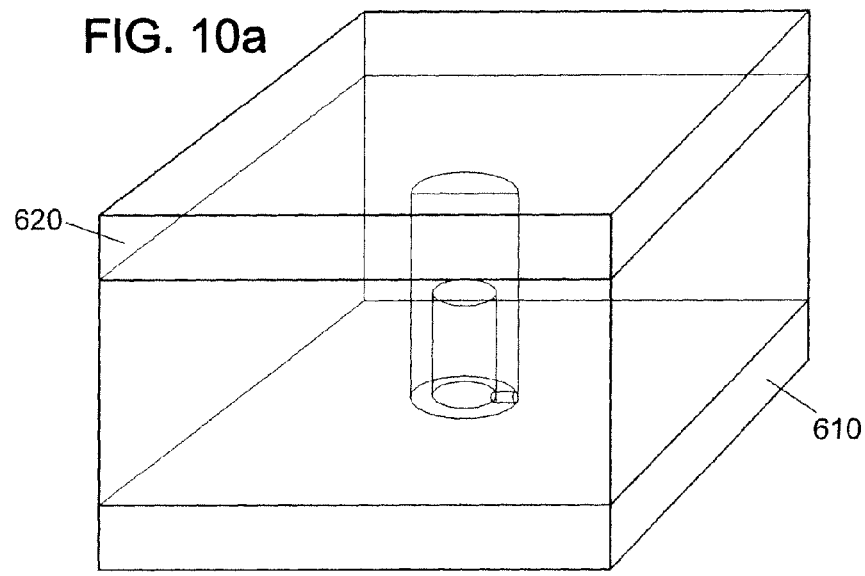
Figure 10B:
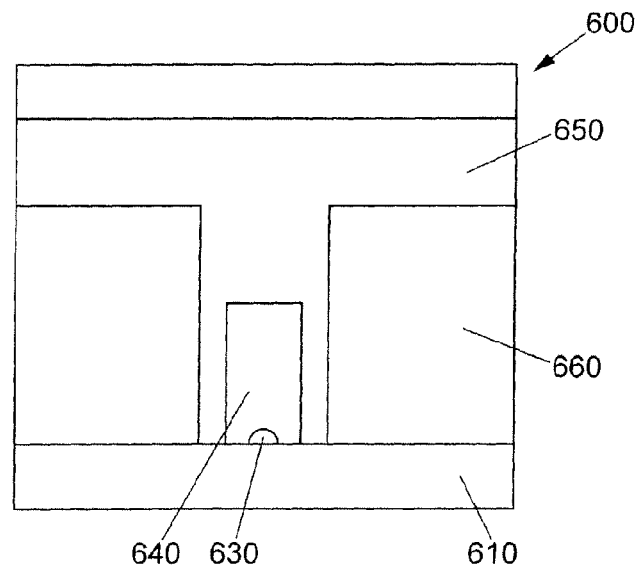

FIGS. 10 a-b illustrate a mould 600 used to manufacture a pillar linear fluidic actuator 205 where a full channel part 630 and a full cylinder 640 are provided on a substrate plate 610. Full part 660 is provided around the full cylinder 640. Full parts may be made of glass. A polymeric material is injected within the bottom substrate plate 610 and an upper plate 620 within the space 650.

According to the manufacturing process of FIGS. 9 and 10, the polymeric part manufactured in FIG. 10 is placed on the polymeric part manufactured in FIG. 9 and pressed on it so that the polymeric material 650 enters in the cylindrical hole formed thanks to cylinder 540. The channels of both parts are connected and thus forming a fluidic inlet for the pillar linear fluidic actuator.

Said steps may be repeated to form an array of pillar linear fluidic actuators. More complex moulds based on the same principle can be provided in order to provide simultaneously a plurality of channels and a plurality of pillars linear fluidic actuators.

Thanks to an adjustable optical device according to the inventions, numerous optical components may be realized, such as adjustable mirrors, adjustable intra ocular lenses and adjustable ophthalmic lenses.

Providing an adjustable optical device (10) to the wearer and adjusting the fluidic pressures (P1, P2 . . . ) of a plurality of internal cavities (210) of the pillar linear fluidic actuators (205) so as to obtain a desired optical system can be widely used. As for examples, such an adjustable optical device can be actuated according to wearer's needs when his environment is varying. Actuation parameters of the adjustable optical device can be provided for examples by the wearer himself, by sensors arranged in the wearer's environment, by an eye care practitioner.

The use of adjustable ophthalmic lenses may also be of great interest when a wearer wants to buy and try new glasses. Test glasses commonly used are currently limited to spherical or cylindrical corrections. Thus an eye care practitioner can up to now only let a wearer test its eye corrections with a limited number of lens configurations where only the lens power and astigmatism can vary.

Thanks to the present invention, an eye care practitioner or optometrist will be able to simulate a wide number of lens configurations by varying the fluidic pressure within the pillar linear fluidic actuators. Complex lens shape may then be achieved and he will be able to offer a "real" test lens to the wearer which could include numerous optical parameters, such as for example asphericity, progressive addition lens (PAL) design characteristics.

He will also be able to offer to the wearer a plurality of test lenses for a given viewer's prescription in order to customize the lens to the wearer's preferences. The viewer will then be able to try the different test lenses made with an adjustable optical device of the invention and to give his opinion. The eye care practitioner can then adjust the parameter and fit the wearer's preferences.

Adjustable parameters may be numerous, and when dealing with PAL, they may include following non limiting parameters: the PAL design; the size parameters of the near vision zone, of the intermediate vision zone, of the distance vision zone; the inset; frame design parameters; head-eye movement ratio; viewing preferences.

The invention has been described above with the aid of embodiments without limitation of the general inventive concept, in particular the adjustable optical device of the invention may be of various shapes and configurations not limited to the examples discussed.

The invention claimed is:

1. An adjustable optical device comprising at least a deformable optical surface activated by linear fluidic actuators, the optical device comprising:
   a material layer comprising an upper surface on which the optical surface is provided and a bottom surface;
   an actuator layer comprising a plurality of linear fluidic actuators separated by at least one cavity, where at least one linear fluidic actuator is a pillar extending in the actuation direction (L) which is non-parallel to the bottom surface of the material layer, said pillar comprising a wall delimiting an internal cavity and where an upper surface of said pillar is continuously linked to a zone of the bottom surface of the material layer; and
   fluidic inlets suitable for introducing a fluid in at least one internal cavity of a pillar linear fluidic actuator,
   wherein the upper surface of the pillar linear fluidic actuator(s) is continuously fixed to the zone of the bottom surface of the material layer by a fixing relationship selected from the group consisting of:
      the pillar linear fluidic actuator(s) and the material layer are made continuously of the same material, and
      the upper surface of the pillar linear fluidic actuator(s) is affixed to the zone of the bottom surface of the material layer.

2. The adjustable optical device of claim 1, wherein the pillar linear fluidic actuator comprises a lower part consisting of the wall and the internal cavity and an upper part situated between the pillar upper surface and the pillar lower part.

3. The adjustable optical device of claim 1, wherein the pillar linear fluidic actuator has a cylindrical external surface which axis extends in the actuation direction L.

4. The adjustable optical device of claim 1, wherein the internal cavity is a cylinder which axis extends in the actuation direction L.

5. The adjustable optical device of claim 1 wherein the thickness of the pillar linear fluidic actuator's wall is between 0.1 to 2 mm.

6. The adjustable optical device of claim 2, wherein the pillar linear fluidic actuator has a cylindrical external surface which axis extends in the actuator direction L, and wherein the height ratio h1/h2 is between 0.2 and 10, where h1 is the highest dimension of the internal cavity at rest according to the L direction and h2 is the distance at rest from the top of the upper surface of the internal cavity to the pillar's upper surface according to the L direction.

7. The adjustable optical device of claim 1 wherein the layer thickness ratio h3/h4 is comprised between 0.1 and 1, where h3 is the highest dimension at rest of the material layer according to the L direction and h4 is the highest dimension at rest of the actuator layer according to the L direction, and where h3 is comprised between 1 to 10 mm.

8. The adjustable optical device of claim 1 wherein the actuator layer is arranged on a substrate layer comprising the fluidic inlets.

9. The adjustable optical device of claim 1, wherein the deformable optical surface is a light reflective surface.

10. The adjustable optical device of claim 1 comprising at least two optical surfaces wherein at least one of said surfaces is actuated by an actuator layer through a material layer and wherein said optical device is light transmissive.

11. A method for adjusting a deformable optical surface of an adjustable optical device according to claim 1, wherein a plurality of fluidic pressures is provided within the internal cavities of the pillar linear fluidic actuators and a constant pressure Po is provided within the cavity(ies) which separate(es) the pillar linear fluidic actuators.

12. A method for providing a lens for a wearer, comprising the steps of:
   providing an adjustable optical device according to claim 10 to the wearer; and
   adjusting the fluidic pressures of a plurality of internal cavities of the pillar linear fluidic actuators so as to obtain a desired optical system.

13. A method for manufacturing an adjustable optical device according to claim 1, comprising the steps of:
   providing a mold with a plurality of closed shapes defining the external contours of the cavities of the linear fluidic actuator layer; and
   providing at least the wall material by moulding.

14. The adjustable optical device of claim 1 wherein the thickness of the pillar linear fluidic actuator's wall is equal or greater to 0.25 mm and/or equal or less to 0.75 mm.

15. The adjustable optical device of claim 4, wherein the pillar linear fluidic actuator has a cylindrical external surface which axis extends in the actuator direction L, and wherein the height ratio h1/h2 is equal or greater to 0.5 and/or equal or less to 2, where h1 is the highest dimension of the internal cavity at rest according to the L direction and h2 is the distance at rest from the top of the upper surface of the internal cavity to the pillar's upper surface according to the L direction.

16. The adjustable optical device of claim 1 wherein the layer thickness ratio h3/h4 is equal or greater to 0.2 and/or equal or less to 0.5, where h3 is the highest dimension at rest of the material layer according to the L direction and h4 is the highest dimension at rest of the actuator layer according to the L direction, and where h3 is equal or greater to 2 mm and/or equal or less to 5 mm.

* * * * *